United States Patent

Sturner et al.

Patent Number: 5,303,327
Date of Patent: Apr. 12, 1994

[54] COMMUNICATION TEST SYSTEM

[75] Inventors: Raymond A. Sturner; James H. Heller; Michael D. Feezor, all of Chapel Hill, N.C.

[73] Assignee: Duke University, Durham, N.C.

[21] Appl. No.: 725,059

[22] Filed: Jul. 2, 1991

[51] Int. Cl.$^5$ .............. G10L 9/02; G09B 7/04
[52] U.S. Cl. .................. 395/2.79; 434/185
[58] Field of Search .............. 381/43, 60, 51; 395/279; 434/167, 169, 176, 185; 73/585, 865.4, 866.3; 128/745, 746

[56] References Cited

U.S. PATENT DOCUMENTS

| | | | |
|---|---|---|---|
| 3,745,674 | 7/1973 | Thompson et al. | 35/9 R |
| 3,784,745 | 1/1974 | Stearns | 179/1 N |
| 3,848,091 | 11/1974 | Stearns et al. | 179/1 N |
| 4,462,411 | 7/1984 | Rickards | 128/746 |
| 4,556,069 | 12/1985 | Dalton. Jr. et al. | 128/746 |
| 4,615,680 | 10/1986 | Tomatis | 434/185 |
| 4,862,505 | 8/1989 | Keith et al. | 381/60 |
| 4,866,778 | 9/1989 | Baker | 381/43 |
| 4,884,447 | 12/1989 | Kemp et al. | 73/585 |
| 4,884,972 | 12/1989 | Gasper | 434/185 |
| 5,009,603 | 4/1991 | Fong et al. | 434/169 |

FOREIGN PATENT DOCUMENTS 58-150829 of 1983 Japan .
1064937 of 1984 U.S.S.R. .

OTHER PUBLICATIONS

Heller et al., 1989 *ASHA Presentation*, Preschool Language Screening Via Interactive Computer, (American Speech and Hearing Association Annual Meeting, St. Louis, Mo.) (Abstract also enclosed), pp. 1-22.

Sturner et al., "Simultaneous Screening for Child Health and Development: A Study of Visual/Developmental Screening of Preschool Children," *Pediatrics* 65, No. 1, pp. 614-621 (1980).

Primary Examiner—Michael R. Fleming
Assistant Examiner—Michelle Doerrler
Attorney, Agent, or Firm—Bell Seltzer Park & Gibson

[57] ABSTRACT

A method of screening communication functions in a human subject comprises (a) presenting a verbal auditory stimulus to the subject, and then (b) scoring a response to the verbal auditory stimulus, with the response being an expressive response, a receptive response, or both. These steps are then cyclically repeated to provide an evaluation of the subject's response to a plurality of verbal auditory stimuli. Once the evaluation is complete, the evaluation is used to determine whether the subject should receive further diagnostic testing. In a preferred embodiment of the invention, subjects are deliberately confounded during the receptive portion of the test.

24 Claims, 5 Drawing Sheets

COMMUNICATION TEST SYSTEM

This invention was made with government support under grant number MCJ-370574 from the United States Public Health Service. The government may have certain rights to this invention.

FIELD OF THE INVENTION

This invention relates to public health in general, and particularly relates to methods and apparatus for testing communication functions such as speech, hearing, and language.

BACKGROUND OF THE INVENTION

Of a child's several developing systems, no other has so profound an impact on his or her total developmental progress as a healthy communication system. Early detection of a deficit in the acquisition of communicative skills is essential because primary language learning is nearly complete by five years of age. Deficits which remain after that age are progressively less responsive to remedial intervention. Unfortunately, while most children are screened for visual or hearing impairment, only a small proportion are screened for communicative disorders. The most common reason for not employing current communicative tests is that they are too time consuming. Accordingly, it would be extremely desirable to have a rapid means for carrying out such tests.

One hearing test device that utilizes words as stimuli has been developed. This instrument was called the Verbal Auditory Screening for Children (VASC). See G. Mecher and B. McCulloch, *Journal of Speech and Hearing Disorders* 35, 241-247 (1970); B. Ritchie and R. Merklein, *Journal of Speech and Hearing Research* 15, 280-286 (1972). In the VASC system, the subject may be asked to identify a picture corresponding to the word presented from a group of pictures, but the subject is not scored for speech and language and the subject's "internal grammar" is not checked for completeness.

U.S. Pat. No. 3,745,674 to Thompson concerns an apparatus for testing the ability of a literate human to distinguish and associate among audio and multiple visual stimuli. Subjects are presented, in synchronization, a sound and a plurality of scenes upon a visual screen, the sound corresponding to one of the scenes presented. The subject responds by selecting a scene and activating a switch which corresponds to the scene selected. The subject is not required to vocalize a phrase presented, and there is no means provided to score the subject's vocalization. The use of masking noise is not suggested. In short, this patent does not describe an apparatus which tests a subject's complete communication system, along with the verbal and visual systems.

U.S. Pat. No. 4,862,005 to Keith et al. discloses an audiometer with an interactive graphic display for testing children. This patent simply describes an audiometer which provides changeable visual reinforcement of favorable responses for the detection of tones, rather than multiple visual images from which the child must choose in response to verbal stimuli. Thus, this apparatus is simply a hearing test, and provides no means to test the subject's communication system.

Another approach to testing hearing is known as SPIN (Speech Perception in Noise). See Kalikow et al., *J. Acoustic Soc. America* 61, 1337-1351 (1977); Bilger et al., *Journal of Speech and Hearing Research* 27, 32-48 (1984). SPIN simulates background conversation speech noise with a "masking" procedure known as babble. In this procedure, the subject is asked to repeat a word presented and the ability to discriminate a picture which corresponds to the word is not tested. The procedure is particularly useful in hearing aid adjustment, but does not provide and is not intended to provide a complete screening test of the communication system.

None of the foregoing tests provides a means for screening young children for communication problems. Accordingly, an object of the present invention is to provide such an apparatus.

Another object of the present invention is to provide a means for screening children for developmental disabilities of the communication system in as routine a manner as visual and hearing screenings are currently conducted.

Another object of the present invention is to provide a means for rapidly determining whether a child should be referred for further diagnostic testing for communication disorders.

SUMMARY OF THE INVENTION

A human communication test apparatus for screening hearing, speech, and language functions in a human subject is disclosed. The apparatus includes a sound generator for presenting a verbal auditory stimulus to a subject, and a video generator operatively associated with said sound generator for presenting a plurality of visual scenes to the subject, with one of the scenes corresponding to the verbal auditory stimulus presented. A first scoring apparatus is operatively associated with the video generator for providing an evaluation of whether the subject can identify the scene corresponding to the verbal auditory stimulus, and a second scoring apparatus is operatively associated with the sound generator for providing an evaluation of the subject's vocalization of the verbal auditory stimulus presented.

Also disclosed is a method of screening communication functions in a human subject. The method comprises, first, presenting a verbal auditory stimulus to the subject; and then scoring a response by the subject to the verbal auditory stimulus. The response may be:

(i) the subject's vocalization of the verbal auditory stimulus presented;

(ii) subject's identification of one scene from a plurality of scenes, wherein only the one scene corresponds to the verbal auditory stimulus presented; or (iii) both (i) and (ii) above.

These steps are cyclically repeated to provide an evaluation of the subject's response to the verbal auditory stimuli. The evaluation is used to determine whether the subject should receive further diagnostic tests of communicative development.

Also disclosed is a method of testing hearing and language functions in a human subject which utilizes deliberately introduced confounds. The method comprises, first, presenting a verbal auditory stimuli to a subject, wherein the verbal auditory stimuli is a test word or test phrase (e.g., a sentence), and then presenting a plurality of visual scenes to said subject. One of the scenes corresponds to the verbal auditory stimulus, and at least one other of the scenes corresponds to a word or phrase differing in sound from said verbal auditory stimuli by a single sound unit (morpheme or phoneme) only. Whether or not the subject can identify the scene which corresponds to the verbal auditory stimulus, in view of the presence of the confound, is then detected.

Numerous additional aspects and embodiments of the foregoing are also disclosed herein, as will be apparent from the specification set forth below.

DETAILED DESCRIPTION OF THE INVENTION

Figure 1:
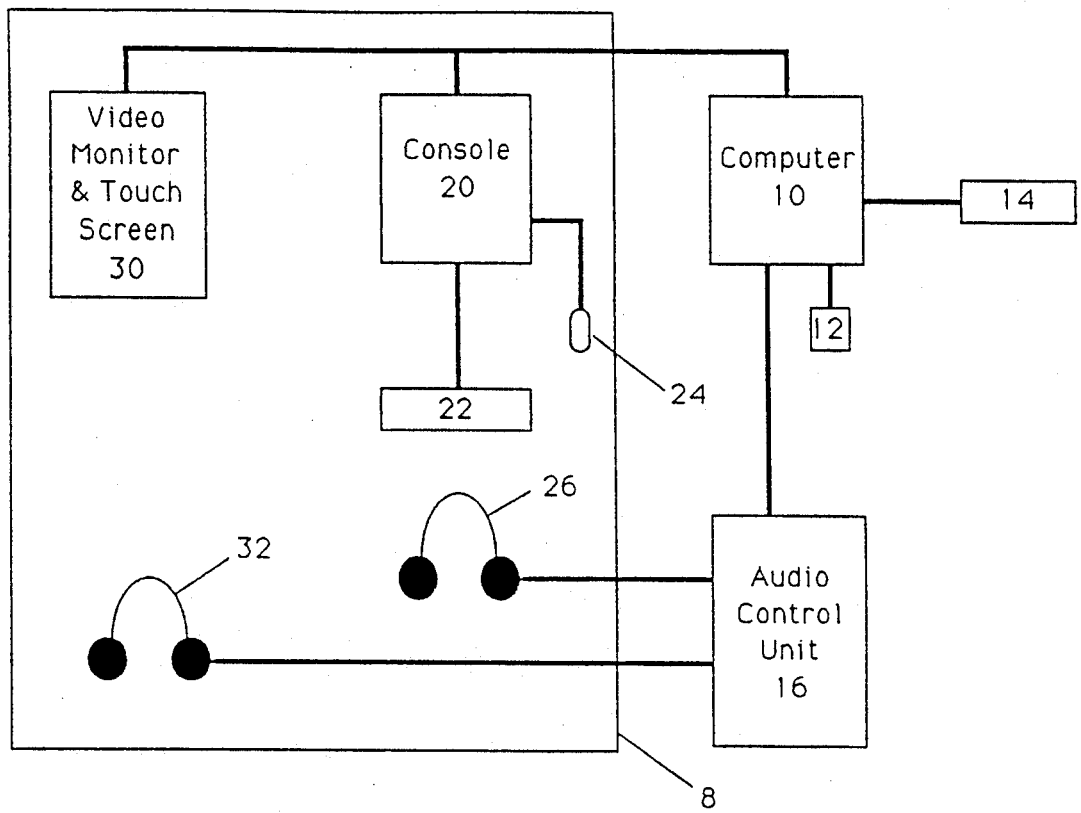
FIG. 1 is a block diagram of a specific embodiment of an apparatus of the present invention.

As used herein, the terms set forth below have the indicated meanings:

"Phoneme" means a speech sound that is a basic unit of spoken language (i.e., the smallest unit of sound in a language which can be distinguished and which serves to differentiate two words). See, e.g., Dorlands Illustrated Medical Dictionary, 1185 (25th Ed. 1974).

"Morpheme" refers to a unit of sound having meaning in the context of language, such as a root word, prefix, suffix, or infix. See Id. at 982. Morphemes and phonemes are referred to collectively herein as "sound units".

"Language" is a system of oral or written symbols used by a group of people with marked consistency in order to communicate.

"Masking noise" refers to any sound used to raise the threshold of audibility of another sound. Examples include white noise, pink noise, and babble.

"Babble" is a masking noise which consists of the concurrent speech of a plurality of speakers simultaneously speaking different passages. A particular type of babble known as "SPIN" babble consists of the speech of twelve trained speakers simultaneously reading different passages.

"Confound" means to deliberately mislead, or lead into error.

As noted above, a method of screening communication functions in a human subject comprises (a) presenting a verbal auditory stimulus to the subject, and then (b) scoring a response to the verbal auditory stimulus, with the response being:

(i) an expressive response (i.e., the subject's vocalization of the verbal auditory stimulus presented);

(ii) a receptive response (i.e., the subject's identification of one scene from a plurality of scenes, wherein only one scene corresponds to the verbal auditory stimulus presented); or (iii) both receptive and expressive responses.

Steps (a) and (b) above are then cyclically repeated to provide an evaluation of the subject's response to a plurality of verbal auditory stimuli. The number of repetitions of the cycle will vary depending upon the particular application of the method and the validity of the particular verbal auditory stimuli presented (i.e., with more valid stimuli, the number of repetitions of the cycle may be reduced). The responses collected are preferably both receptive and expressive, though they need not and preferably are not collected simultaneously for each verbal auditory stimulus. In the alternative, only receptive or only expressive responses may be collected for particular tests in particular environments, as discussed in greater detail below. Once the evaluation is complete, the evaluation is used to determine whether the subject should receive further diagnostic testing (also discussed below).

A human communication test apparatus for carrying out the foregoing method includes a sound generator means, a video generator means, first scoring means, and second scoring means. As discussed below, all of these may be peripheral devices connected to a suitable controller, such as a personal computer, with a software program running in the computer to operatively associate the respective components and carry out coordinated operation of the testing methods described herein. A specific example of this apparatus is discussed in Example 1 below, with the apparatus being discussed in general terms immediately below.

A sound generator means may be comprised of a storage device such as a tape recording or digitized sound stored in a memory device. The sound generator means should also include a set of headphones or other sound reproduction device associated with the storage device for presenting the verbal auditory stimulus to either or both ears of the subject. A second set of headphones (or other sound reproduction device) may be provided for presenting the stimulus to an operator, with or without the sound degredation presented to the subject, as discussed in greater detail below, though the operator may be given the stimulus in visual form (i.e., by displaying the word or phrase presented to the subject in visual form as words on a video display terminal operatively associated with the sound generator. Preferably, the sound generator means comprises a computer-controlled precision speech audiometer with ear switching and soft turn-on and turn-off.

A video generator means associated with the sound generator means may be comprised of an image stored on a storage device connected to the controller, such as a video tape, an optical disc (i.e., a CD ROM), or a hard drive or other storage device. A video display terminal is connected to the storage device to display the stored image to the subject. Video displays other than terminals, such as projection displays, are also suitable. The video generator means should be operatively associated with the sound generator means so that a plurality of visual scenes are presented to the subject in conjunction with the verbal auditory stimulus, with only one of the scenes corresponding to the verbal auditory stimulus presented. Any number of scenes may be presented, but we have found four scenes presented one per quadrant on a video display terminal particularly suitable.

A first scoring means operatively associated with the video generator means for providing an evaluation of whether the subject can identify the scene corresponding to the verbal auditory stimulus is preferably a touch screen input device mounted over the video display terminal, with the touch screen connected to the controller, so that the subject can select a particular scene by touching the image as it appears on the video display. Alternative arrangements, such as a light pen, mouse or other pointing device, or a series of switches separate from the video display with a predetermined switch associated with a predetermined region of the video display, may also be employed.

A second scoring means for providing an evaluation of the subject's vocalization of the verbal auditory stimulus presented is preferably a human-operated keyboard, mouse, light-pen, or other input device connected to the controller. The human operator may be provided with a separate video display terminal connected to the controller for use in association with the input device, with a software program running in the controller providing the appropriate displays on the video terminal for carrying out the scoring of the subject's vocalization of the particular verbal auditory stimulus presented. Preferably, means for scoring the production of individual sound units of the verbal auditory stimulus by said subject are provided, such as a separate input for each phoneme of a word when a word is the verbal auditory stimulus, or inputs for some or all of the morphemes of a phrase when a phrase is the verbal auditory stimulus.

A storage means operatively associated with the first and second scoring means for storing the evaluation of whether the subject can identify the scene corresponding to the verbal auditory stimulus and the evaluation of the subject's vocalization is preferably a magnetic storage unit such as a hard disk connected to the controller. Again, other storage devices may also be used.

The apparatus of the present invention may include a processor for determining whether the subject should receive further diagnostic tests based upon the evaluation of whether the subject can identify the scene corresponding to the verbal auditory stimulus and the evaluation of the subject's vocalization. The processor may be a software program running in the controller. The processor may include an empirically based model of actual clinical experience (such as a statistical model, or more particularly a stochastic model) to determine whether the subject should receive further diagnostic tests. Since an object of the present invention is to provide a rapid screening test, rather than a thorough diagnostic evaluation, the processor preferably provides simply a "yes" or "no" answer to the question of whether or not the subject should receive further diagnostic tests for disorders of the subject's communicative system (i.e., hearing, speech, and language).

A problem with current speech and language tests is that few (if any) tests have scoring procedures for more than one subculture (i.e., tests which account for regional dialects). The cost of obtaining the "local norms" necessary to obviate this problem have heretofore been prohibitive. The present invention can solve this problem by including a data file of actual clinical experience (e.g., a remote database on the storage device of a central computer, with the computer containing the necessary interfacing software), with the apparatus including means such as a modem or data output program for communicating with the data file for adding the evaluations of the subject to the data file. The empirically based model of actual clinical experience can then be derived from the central data file. This allows continuous updating of the empirically based model as new data is collected, and enhances the ability to adapt the empirical model to local norms once sufficient data is collected in a particular region or for a particular subculture. Note that a plurality of testing apparatus described above can be associated with a single central data file.

If the processor is to provide an indication of whether the subject should receive further testing based upon local norms, then demographic data concerning the subject is preferably collected. To collect such data, the apparatus should include means for recording demographic data concerning the subject such as a keyboard and appropriate software program routines in the controller, and the processor should use the demographic data in connection with the empirical model to determine whether the subject should receive further diagnostic tests. Appropriate demographic data to collect from the subject may include some or all of the following: age; whether the language of the verbal auditory stimuli is the subject's first language; sex; ethnic group; and geographic location.

A unique aspect of the present invention is that, when visual scenes are presented to the subject, the scenes are selected to confound the subject Thus, where the verbal auditory stimulus comprises a test word (e.g., "cat"), one of the scenes corresponds to said test word (e.g., a picture of a cat), and at least one other of the scenes corresponds to a second word differing in sound from the test word by a single phoneme only (e.g., a picture of a bat; the word "bat"). When the verbal auditory stimulus comprises a test phrase (e.g., "where is the mouse"), one of the scenes corresponds to the test phrase (e.g., a picture of a mouse in a box), and at least one other of the scenes corresponds to a second phrase differing in meaning from the test phrase by a single morpheme only (e.g., a picture of two mice in a box). With respect to test phrases, in a preferred embodiment of the invention, two morphemes in the test phrase are varied to generate four scenes, only one of which is correct. For example, if the test phrase is "where are those kittens", then the scenes can show: (a) single kitten; (b) single mouse; (c) plural kittens (correct); and (d) plural mice.

In a preferred embodiment of the invention, the verbal auditory stimulus is degraded to make it more difficult for the subject to make a correct response. This may be carried out by filtering speech (enhancing or reducing parts of the spectrum); chopping words temporally and presenting different segments to different ears; or presenting the stimulus with a masking noise (preferably babble such as SPIN babble). The apparatus should include the appropriate filters, circuitry, or noise generators for carrying out degradation of the stimulus.

The apparatus described above may be modified to suit particular environments, such as a physician's office or a school setting, where testing procedures may differ. Thus, the scoring of the subject's vocalization might be eliminated from a particular apparatus, or the generation and scoring of visual scenes might be eliminated from a particular apparatus, depending upon the specific tests and purpose for which the apparatus is intended. In addition, while the method and apparatus disclosed herein are intended initially for pediatric screening, those skilled in the art will appreciate that they may be adapted for screening and testing older children and adults for various purposes.

While the apparatus described above contemplates the use of a human operator, those skilled in the art will appreciate that test may be entirely automated through the incorporation of speech recognition apparatus. An example of a speech recognition apparatus is disclosed in U.S. Pat. No. 4,866,778 to Baker (the disclosure of which applicants is incorporated herein by reference). Such apparatus could be incorporated into the present invention as a means for detecting the subject's verbal communications.

The present invention is explained in greater detail in the following non-limiting examples.

EXAMPLE 1

A Pediatric Communication Screening System

FIG. 1 is a block diagram of a specific embodiment of the present invention. As shown in FIG. 1, a computer 10, controls and receives input from a video monitor having a touch screen mounted thereon 30. The computer 10 controls the image presented to the test subject on the video monitor 30 to prompt the test subject to vocalize the verbal auditory stimulus or to select the image on the video monitor which corresponds to the verbal auditory stimulus. The touch screen 30 accepts the selection input of the test subject when the test subject is requested to select the image which corresponds to the verbal auditory stimulus. The verbal auditory stimulus is generated by software executing within the computer 10 and is presented to the test subject through headphones 32. The verbal auditory stimulus is also presented to the examiner through headphones 26. The amplitude of the verbal auditory stimulus is controlled by the audio control unit 16. The audio control unit 16 also combines the verbal auditory stimulus with a masking noise. The method of masking and amplitude of masking noise are selected within the audio control unit 16.

For scoring the responses of the test subject, a console 20 is provided for the examiner. Associated with the console 20 is a keyboard 22 and a pointing device 24 such as a mouse. The console 20 and associated devices are utilized by the examiner to input information about the test subject and the responses the test subject provides to the verbal auditory stimulus. The scoring information input by the examiner and the corresponding selection information from the touch screen 30 are recorded by the computer 10. The computer 10 has associated with it a disk drive 12 on which data and program information can be stored. The computer 10 may also optionally have a printer 14 attached so as to provide printed output of test results.

The computer 10 may be any stored program control processor capable of controlling multiple input and output devices. A personal computer such as the Gateway 2000 personal computer (North Sioux City, S.D.), utilizing the Intel 80386 microprocessor is desirable because of the increased processing speed of the 80386 microprocessor however other computers known to one skilled in the art may be used. The video monitor and touch screen 30 may be comprised of an NEC Multisync 3D or other high resolution video monitor in combination with a touch screen input device such as those manufactured by Interactive Systems of Watertown, Mass. The video monitor is controlled by a graphics adapter card of the computer 10. Suitable graphics adapters include the VGA Wondercard graphics adapter and other high resolution graphics devices such as IBM 8514A graphics devices, and S-VGA devices. The console 20 and associated input devices 22 and 24 may be comprised of a monochrome video monitor and suitable monochrome adapter card (both available from Jameco Electronic Components of Belmont, Calif.), the keyboard associated with the Gateway 2000 personal computer and a Microsoft Mouse available from Microsoft Corp. of Redmond, Wa.

The audio portion may comprise a Computer Controlled Speech Presentaion device, an Audiometer with Babble Masking produced by Electronic Design Consultants and a Peripheral Digital Interface PIO-12 manufactured by of Taunton, Mass. The speech is digitized using the 16-bit digital format that has become a standard for compact disks. The data rate used is 48K samples/second, somewhat higher than the standard, which allows recovery of an 18 kHz bandwidth of sound without brickwall antialiasing filters. The quality and integrity of this system is verified from record to playback using sine and triangular waves. The bandwidth and dynamic range measures 18 kHz for the former and about 90 dB for the latter.

Improved performance of the above described apparatus may be achieved through the use of direct memory access (DMA) which decreases the memory access time of the computer 10 and thereby increases the performance of the apparatus. Accordingly, DMA controllers such as the Direct Memory Access DMA-16 manufactured by MetraByte may be used.

The headphones 32 for the test subject may be Sony MDRV2 headphones, or other headphones suitable for reducing the amount of ambient sound heard by the test subject. The headphones 26 for the operator may be Radio Shack RS20 headphones or other suitable headphones.

Figure 2:
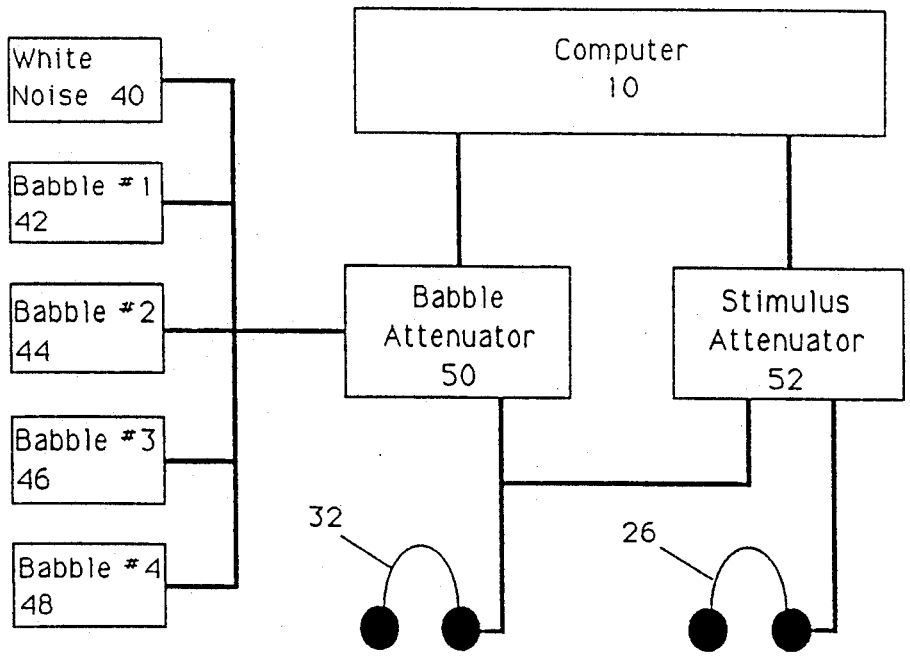
FIG. 2 is a more detailed block diagram of the verbal auditory stimulus presentation section of the apparatus of FIG. 1.

FIG. 2 is a more detailed block diagram of the verbal auditory stimulus presentation section of the embodiment of the present invention illustrated in FIG. 1. The computer 10 presents a digitized word or phrase to the stimulus attenuator 52 which adjusts the amplitude of the stimulus and presents the stimulus to the headphones 32 of the test subject and the headphones 26 of the examiner. The babble attenuator 50 receives input from the computer 10 to control the amplitude of the masking signal and receives the masking signal from the masking sources 40, 42, 44, 46 and 48. The babble attenuator 50 adjusts the amplitude of the masking signal from the selected mask source and presents the masking signal to the headphones 32 of the test subject substantially simultaneously with the presentation of stimulus. In this apparatus four different babble sequences are available from masking sources 42, 44, 46 and 48 and may be individually selected under control of the computer 10 as required, though only one masking source need be used to carry out the methods disclosed herein.

Figure 3A:
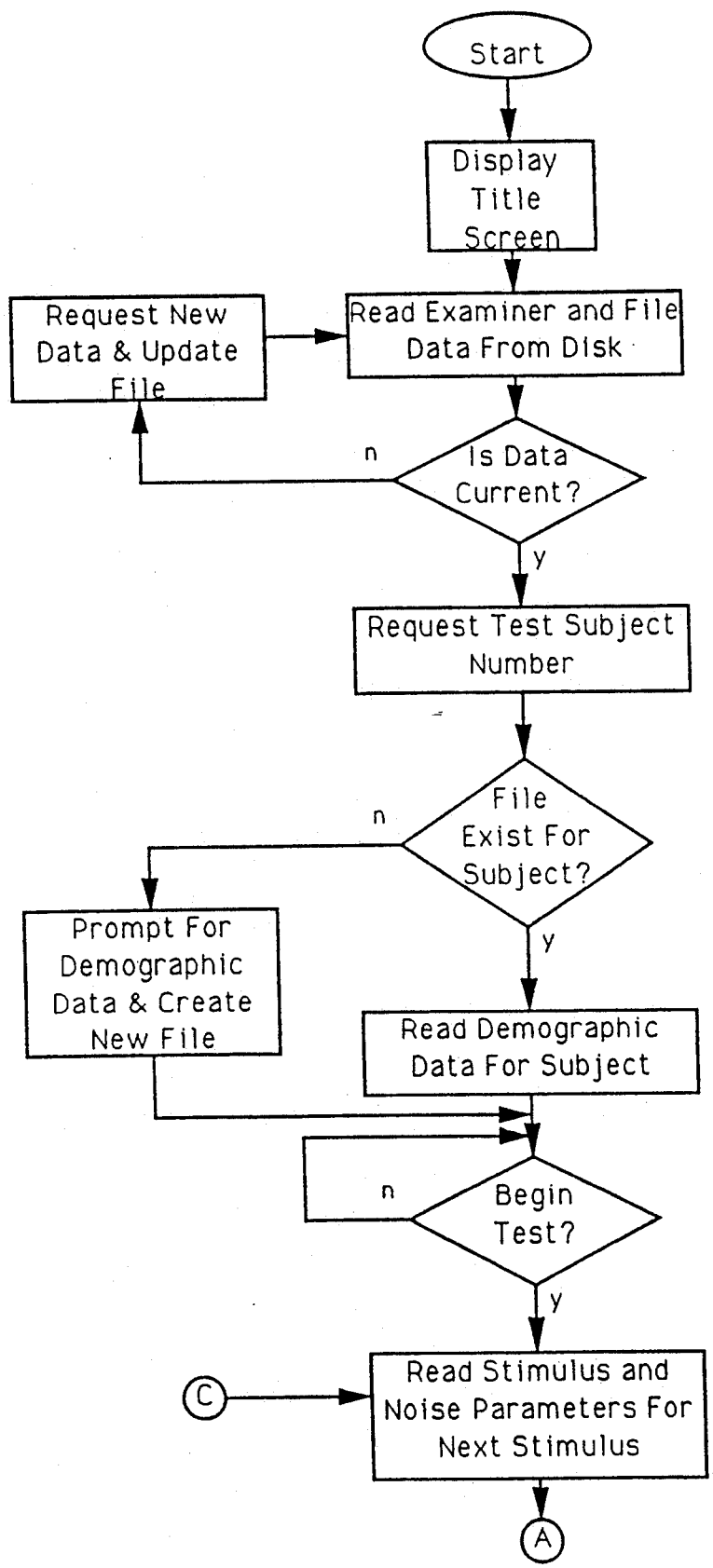
FIGS. 3A through 3C are a flow diagram of the software which controls the operation of the apparatus described in FIGS. 1 and 2 above.
Figure 3B:
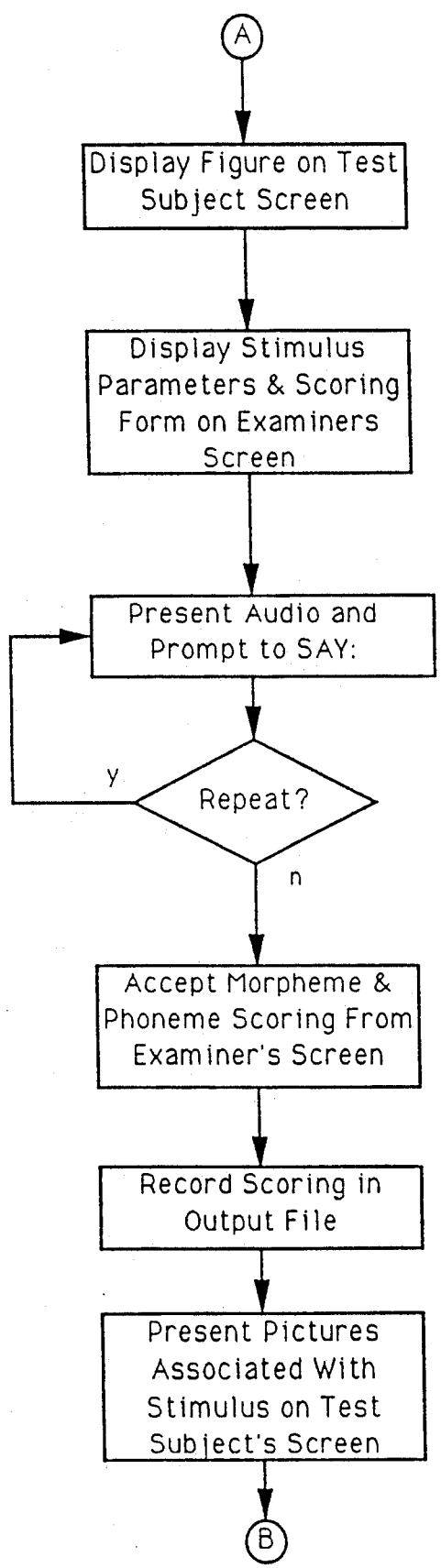
Figure 3C:
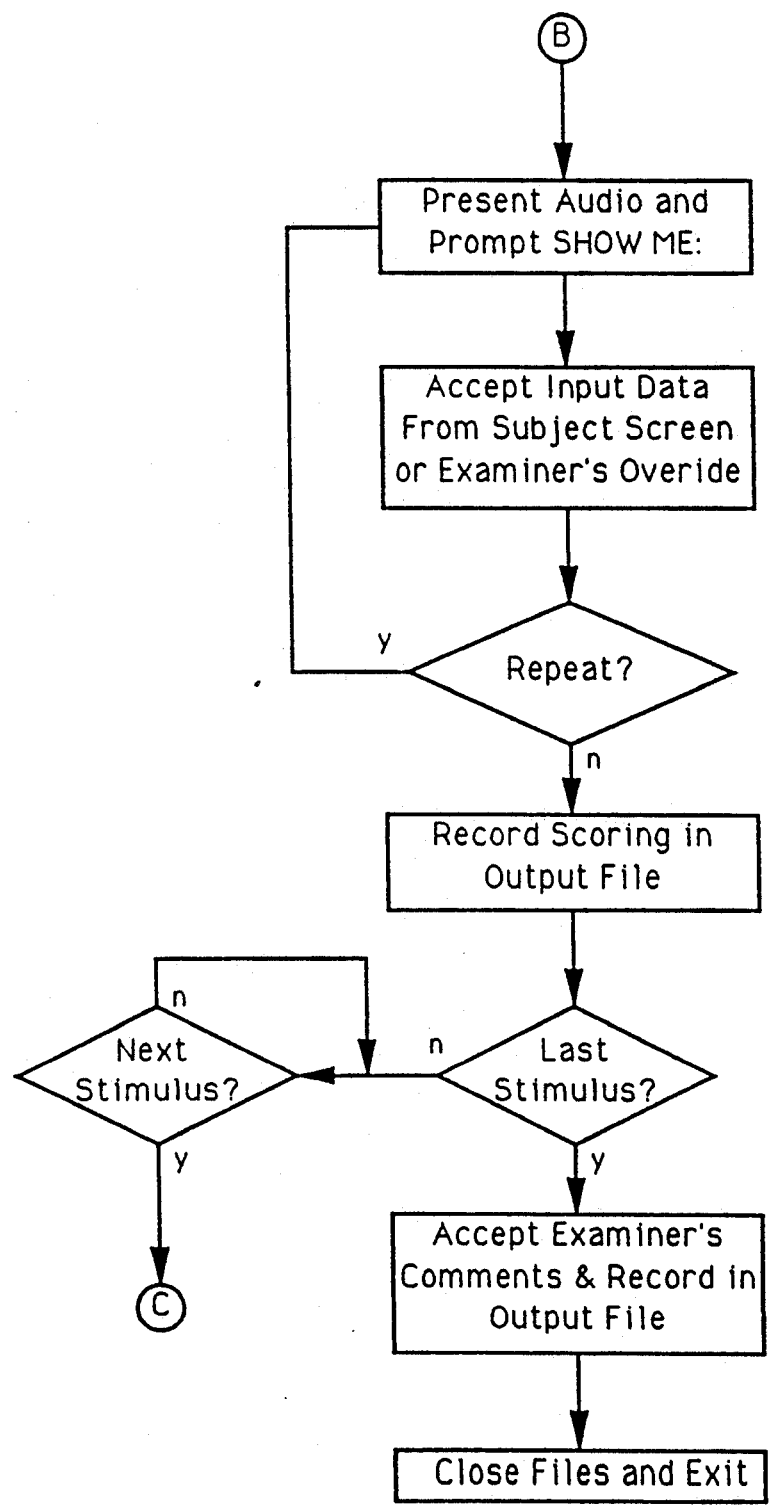

FIGS. 3A through 3C are a flow diagram of the software which controls the operation of the above described apparatus. As is seen in FIG. 3A, after initially displaying a title screen on the console 20, information about the examiner and the files to be used during the examination is retrieved from the hard disk 12. The examiner is then asked if the data is current. If the response indicates that the information is not current the new data is requested and the file stored on the hard disk 12 is updated. If the response of the examiner indicates that the data is current, the examiner is requested to input the test number of the test subject. If information is already stored on disk for the test subject then that information is retrieved. If no information exists on the test subject the examiner is prompted to input the test subject data and that data is stored on disk.

When the examiner and test subject are ready to begin the test, the following steps are repeated for each verbal auditory stimulus until all the stimuli have been utilized. The stimulus and masking parameters are read from disk. The test subject is then prompted by a figure on the test subject video monitor 30 to repeat the verbal auditory stimulus. The stimulus and scoring form are presented to the examiner on the console 20. The verbal auditory stimulus and any masking noise are then presented to the test subject. The test subject then verbalizes the stimulus and the examiner scores the verbalization using the input devices 22 and 24. The examiner is then prompted to determine if it is necessary to prompt the test subject again. If the response of the examiner is in the affirmative, then the stimulus is presented and the test subject is again prompted to repeat the stimulus. If the response is in the negative, then the scoring input is read from the console 20 and then stored in the file associated with the particular test subject on the disk 12. Multiple visual images are then presented on the test subject video monitor 30. The verbal auditory stimulus and masking noise are then presented to the test subject and the test subject is prompted to select the image which corresponds to the verbal auditory stimulus. Input is then accepted from the touch screen 30 or from the examiner's console 20 representing the image selected by the test subject. The examiner is then prompted to determine if it is necessary to prompt the test subject again. If the response of the examiner is in the affirmative, then the stimulus is presented and the test subject is again prompted to repeat the stimulus. If the response is in the negative, then the response is then stored in the file associated with the particular test subject on the disk 12. The preceeding steps are repeated for each stimulus until the final stimulus is reached.

After completing the above for each stimulus, the examiner is prompted for any comments which are recorded in the test subject's file on the disk 12. Then all files are closed and the program is terminated.

As described above, information about the test site is retained when the system is powered down and does not have to be altered until the test site is changed, thereby permitting testing with a minimum of overhead for entry of demographic data. Once data for a given test subject has been entered, it does not need to be re-entered. In the event of a re-test, the system will identify that subject and recall the subject's disk file. The data from the new test is concatenated with the results of the previous test so that only one file is maintained per subject.

The program includes the display of a clown in a "listening" pose, together with an audible prompt "say" to prompt the test subject to repeat the verbal auditory stimulus. Following this presentation, four images are displayed on the test subject video monitor 30. The console 20 screen keeps the examiner fully informed about the progress of the test. The audio and video stimuli are identified on the screen along with the level of the audio stimulus and masking presentations. The examiner may increase the masking level during the receptive task.

The stimulus, word or sentence, presented to the test subject is displayed on the console 20 screen with scoring boxes for morphemes located above the line, and scoring boxes for phonemes located below the line. Scoring may be accomplished rapidly by moving the mouse 24 controlled cursor to a given box and clicking the mouse button to indicate an error. The mouse cursor can also be used with other displayed boxes to indicate "no response," to repeat an audio presentation, to advance to the next stimulus item, and to override a touch screen response which the test subject indicates to be a mistake.

EXAMPLES 2

Validation Study with Hearing-Impaired Children

This study shows that apparatus described in Example 1 above can be used to identify test items which discriminate children with normal hearing and normal middle ear function from those with hearing impairment and with abnormal middle ear function. Note that items identified in this study can be pooled with items identified in the articulation and language validation studies for use on subsequent large population validation studies, and to provide an empirical database of actual clinical experience as discussed above.

A. METHODS

Subjects: The subjects are placed in one of the following groups based on hearing acuity of the test ear:
  (1) Normal hearing: children whose hearing sensitivity is better than or equal to 20 dB HL at 500, 1.0k, 2.0k and 4.0k Hz.
  (2) Mild conductive loss: children whose
  pure tone threshold average is between 20 dB HL to 30 dB HL due to a conductive loss as measured in a standard audiological evaluation.

The subjects are also grouped according to middle ear status as evidenced by tympanogram. See J. Jerger, Arch. Octolaryng. 92, 311-324 (1970):
  (1) Normal compliance: (Type A) Middle ear pressure greater than or equal to −150.
  (2) Middle ear fluid: (Type B) Flat tympanogram, the absence of a pressure peak.

Each child is placed in one of four age groups: Group I, ages 3 years 6 months old to 3 years, 11 months old; Group II, ages 4 years 0 months to 4 years 5 months; Group III, ages 4 years 6 months to 4 years 11 months; and Group IV, ages 5 years 0 months to 5 years 5 months. Children in the mild sensori-neural and moderate loss groups are not grouped according to age.

Impedance: The subjects in the normal hearing group and the mild sensori-neural hearing impaired group have normal eardrum compliance as evidenced by a Type A tympanogram. See J. Jerger, Arch. Otolaryng. 92, 311-324 (1970). The subjects in the mild conductive hearing group and the mixed grouped have abnormal eardrum compliance, i.e., Type B or Type C tympanograms and are not required to meet any criterion for normal eardrum compliance.

Design: Children are assigned to one of four groups according to their hearing ability, as described above. The test stimuli are presented to the children via headphone to the identified ear. Only one ear is tested per child; test ear is counterbalanced.

Procedure: The test stimuli consist of 51 items: 28 words and 23 sentences (see Tables 1 and 2 below). The stimuli are presented first expressively, where the child is required to repeat the target word or sentence. This is followed by a receptive presentation of the same stimulus. The child is required to point to the picture of the test item that is presented to him. In the expressive portion of the test a picture of a clown appears on the test system computer monitor to capture the child's visual attention. The child is instructed that the clown will say the word (or sentence) that the child is to repeat. The test stimulus includes the carrier phrase "say" presented at the same intensity as the test stimulus without background noise.

The child's verbal response is scored by the examiner for both articulation and language content. When the examiner is finished scoring he or she pushes a button indicating the start of the receptive portion of the test. Four pictures are presented on the monitor, and the child is told to point to the picture that he hears.

Figure 4:
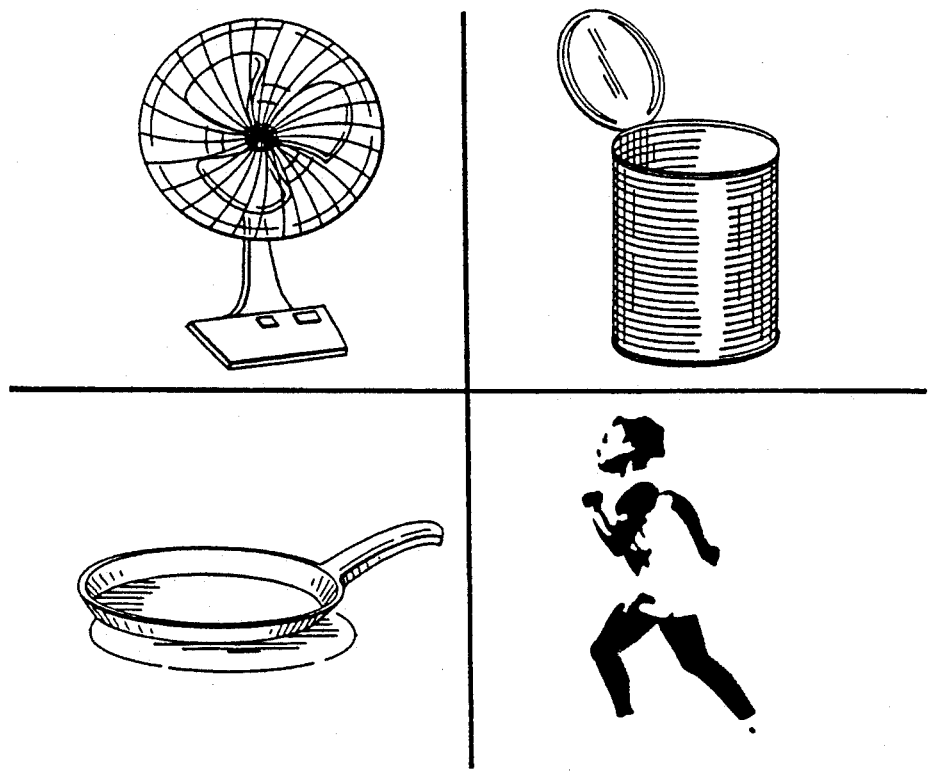
FIG. 4 is illustrative of scenes which may be presented to a subject in conjunction with a verbal auditory stimulus comprising a word.

For example, if the test item is "fan", then the pictures presented could be those shown in FIG. 4, namely, a fan (top left), can (top right), pan (bottom left), and "ran" (bottom right). Note that the correct picture is the picture of the fan, while the incorrect pictures correspond to words which differ from the test item by one phoneme only.

Figure 5:
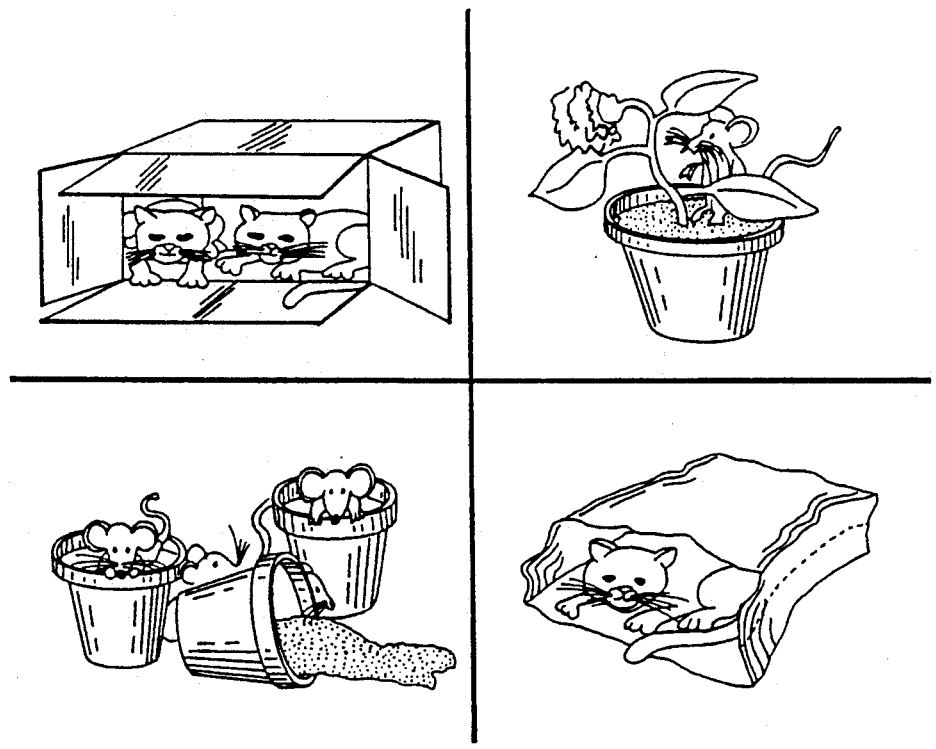
FIG. 5 is illustrative of scenes which may be presented to a subject in conjunction with a verbal auditory stimulus comprising a sentence.

As another example, if the test item is "where are those kittens? " then the pictures presented could be those shown in FIG. 5, namely, a plurality of kittens (top left), a single mouse (top right), a plurality of mice (bottom left), and a single kitten (bottom right). Note that the correct picture is the picture of the plurality of kittens, while two of the other three pictures (the single kitten and the plurality of mice) correspond to phrases which differ from the test item by one morpheme only.

The receptive test items are preceded by "show me" which is also presented at 35 dB HL without noise. The test stimuli are always presented at 35 dB HL. In the expressive portion of the test the babble is presented at 25 dB, resulting in a signal-to-noise ratio of +10. In the receptive portion of the test the stimuli is presented at 35 dB, and noise is presented at 30 dB, resulting in a signal-to-noise ratio of +5.

Following tympanometry the child is taken into the audiological booth and trained on the test system. Training includes two live voice presentations of the expressive and receptive tasks with single syllable words. The child is instructed to say the word, e.g., teeth, and then to find the picture of the teeth in a group of four pictures. Following the presentation of the second live voice training item the child begins training on the computer.

Computer Training: The child is trained on a series of five test words presented expressively and receptively. The five training words include: mad, wake, cat, goat, and chin. The words mad and wake are presented at 35 dB HL with no noise. Cat and goat are presented at 35 dB HL with 20 dB HL of babble. Chin is presented expressively at 35 dB HL with 25 dB HL of babble. Feedback is provided on each training item and correct performance is demonstrated when an error is made. Following training word testing is begun immediately. The clown continues to appear on the computer monitor to signal the expressive item. Expressive items are presented at 35 dB HL with babble at 25 dB HL. Receptive items are presented at 35 dB HL with babble at 30 dB HL. No feedback for the test items responses is provided.

Following the administration of the 28 word stimuli the child is presented two training sentences at 35 dB HL with noise at 35 dB HL. The training sentences include: "The boy is sitting on the chair" and "the deer is eating." Feedback is provided for these items. After the two sentence training items are completed the 23 test sentences are presented. The word and the sentence test stimuli are presented in random order, within set, as specified by the test protocol software described above.

Expressive word stimuli are evaluated for the correct production of the consonants and the vowel in the word. Expressive sentence stimuli are evaluated on the correct production of each morpheme of the sentence and the production of a few articulation targets for each sentence. Scoring of expression targets is completed by the examiner. Scoring on the receptive picture identification response (touch screen) is performed by computer.

B RESULTS

Receptive Component of the Communication Screening System: For each word and sentence stimulus on the system, the child is presented with four pictures and instructed to show the examiner the one best representing the stimulus by touching the appropriate picture on the computer screen. The child's response is recorded by the computer and is scored as either correct (score of 1) or incorrect (0). To examine the ability of this receptive portion of the Screening System to identify hearing problems, children with Type A tympanograms were compared to those with Type B using these "receptive" scores, and children passing the hearing test were compared to those failing it. Tables 1 and 2 present the percentage of children with Type A and B tympanograms and of those passing and failing the hearing screen who correctly identified each word or sentence stimulus. Nine of the 28 words (32%) and 7 of the 23 sentences (30%) significantly (p<0.05) differentiated either the Type A and B groups or the two hearing groups. An additional 11% of the words and 26% of the sentences showed at least modest ability to discriminate the groups (p<0.10).

Expressive Component of the Communication Screening System: In addition to selecting the picture representing each stimulus, the child was asked to "say" (repeat aloud) each stimulus word or sentence. These utterances form the expressive component of the test. Analyses examined each individual morpheme and phoneme as well as language and articulation scores for each word, each sentence, the set of words, and the set of sentences.

A significant difference in performance between normal hearing and hearing-impaired groups (p<0.05) was noted on 25% of the individual word phonemes and 35% of the sentence phonemes. A significant difference in performance between normal (type A) and middle ear fluid groups (type B) was noted on 23% of the individual word phonemes and 32% of the sentence phonemes.

TABLE 1

Percent of Children with Type A and B Tympanogram and Passing and Failing Diagnostic Hearing Testing who Selected the Correct Picture for Each Word Stimulus

| STIMULI Test Words | TYMPANOGRAM RESULT | | HEARING DIAGNOSTIC RESULT | |
|---|---|---|---|---|
| | Type A % Corr (n = 34) | Type B % Corr (n = 18) | Pass % Corr (n = 37) | Fail % Corr (n = 13)[a] |
| 6. catch | 91.2 | 82.4 | 94.6 | 76.9 |
| 7. bath | 38.2 | 27.8 | 40.5 | 23.1 |
| 8. bees | 88.2 | 66.7[c] | 86.5 | 69.2 |
| 9. seal | 91.2 | 61.6[b] | 91.9 | 53.8[b] |
| 10. sneeze | 67.6 | 55.6 | 67.6 | 61.5 |

TABLE 1-continued

Percent of Children with Type A and B Tympanogram and Passing and Failing Diagnostic Hearing Testing who Selected the Correct Picture for Each Word Stimulus

| STIMULI Test Words | TYMPANOGRAM RESULT | | HEARING DIAGNOSTIC RESULT | |
|---|---|---|---|---|
| | Type A % Corr (n = 34) | Type B % Corr (n = 18) | Pass % Corr (n = 37) | Fail % Corr (n = 13)[a] |
| 11. nail | 41.2 | 33.3 | 43.2 | 30.8 |
| 12. clock | 50.0 | 38.9 | 51.4 | 38.5 |
| 13. run | 76.5 | 72.2 | 75.7 | 76.9 |
| 14. fan | 29.4 | 33.3 | 32.4 | 23.1 |
| 15. ship | 73.5 | 61.1 | 75.7 | 53.8 |
| 16. pea | 64.7 | 38.9[c] | 67.6 | 23.1[b] |
| 17. chick | 73.5 | 50.0[c] | 75.7 | 46.2[c] |
| 18. pot | 73.5 | 22.2[b] | 70.3 | 23.1[b] |
| 19. bone | 94.1 | 44.4[b] | 91.9 | 38.5[b] |
| 20. beach | 91.2 | 77.8 | 91.9 | 69.2[c] |
| 21. leaf | 88.2 | 38.9[b] | 83.8 | 38.5[b] |
| 22. ran | 23.5 | 11.1 | 21.6 | 15.4 |
| 23. whale | 50.0 | 38.9 | 46.0 | 53.8 |
| 24. lock | 58.8 | 44.4 | 62.2 | 38.5 |
| 25. jail | 94.1 | 77.8 | 94.6 | 69.2[b] |
| 26. keys | 88.2 | 77.8 | 89.2 | 76.9 |
| 27. snail | 82.4 | 55.6 | 83.8 | 53.8[b] |
| 28. chair | 58.8 | 66.7 | 59.5 | 69.2 |
| 29. choke | 70.6 | 61.1 | 73.0 | 61.5 |
| 30. rat | 76.5 | 55.6 | 81.1 | 46.2[b] |
| 31. spot | 58.8 | 50.0 | 62.2 | 46.2 |
| 32. tear (cry) | 64.7 | 66.8 | 73.0 | 53.8 |
| 33. sad | 76.5 | 50.0[c] | 78.4 | 30.8[b] |

[a] Two children did not have diagnostic hearing results.
[b] $p < .05$, 1 t. Fisher's Exact Test for Type A vs. Type B and Hearing Pass vs. Fail
[c] $p < .10$, 1 t. Fisher's Exact Test for Type A vs. Type B and Hearing Pass vs. Fail

TABLE 2

Percent of Children with Type A and B Tympanogram and Passing and Failing Diagnostic Hearing Testing who Selected the Correct Picture for Each Sentence Stimulus

| STIMULI Test Sentences | TYMPANOGRAM RESULT | | HEARING DIAGNOSTIC RESULT | |
|---|---|---|---|---|
| | Type A % Corr (n = 34) | Type B % Corr (n = 18) | Pass % Corr (n = 37) | Fail % Corr (n = 13)[a] |
| 36. Mother says, "Look who is here." | 73.5 | 61.1 | 70.3 | 69.2 |
| 37. It is not time to go to school. | 32.4 | 35.3 | 32.4 | 38.5 |
| 38. Push the broken wagon. | 64.7 | 50.0 | 67.6 | 38.5[c] |
| 39. The train hits the car. | 73.5 | 50.0[c] | 73.0 | 38.5[b] |
| 40. What is she looking for? | 73.5 | 50.0[c] | 75.7 | 46.2[c] |
| 41. Mother says, "Who is that girl?" | 61.8 | 33.3[c] | 62.2 | 30.8[c] |
| 42. The boy sees himself. | 76.5 | 33.3[b] | 73.0 | 30.8[b] |
| 43. Look at the lazy clown. | 52.9 | 55.6 | 54.0 | 61.5 |
| 44. Mother says, "Look what is here." | 58.8 | 44.4 | 59.5 | 38.5 |
| 45. Isn't that a funny skater. | 61.8 | 29.4[b] | 56.8 | 30.8 |
| 46. We saw flying fish at the zoo. | 55.9 | 52.9 | 56.8 | 53.9 |
| 47. They walked into the store to buy his books. | 41.2 | 52.9 | 46.0 | 41.7 |
| 48. Where are those kittens? | 76.5 | 38.9[b] | 73.0 | 38.5[b] |
| 49. This is a sunny day. | 70.6 | 33.3[b] | 67.6 | 38.5[c] |
| 50. Thank you for my present. | 76.5 | 55.6 | 75.7 | 61.5 |
| 51. The car hits the train. | 67.7 | 38.9[b] | 67.6 | 38.5[c] |
| 52. The boy sees the shelf. | 41.2 | 27.8 | 43.2 | 15.4[c] |
| 53. Some bluebirds are eating the seed. | 38.2 | 22.2 | 37.8 | 23.1 |
| 54. There is a big ball in the box. | 67.7 | 55.6 | 64.9 | 69.2 |
| 55. Now I'll plant the bushes and trees. | 52.9 | 44.4 | 56.8 | 30.8[c] |
| 56. I don't know why he's crying. | 58.8 | 22.2[b] | 56.8 | 15.4[b] |
| 57. Mother says, "Where is that girl." | 58.8 | 38.9 | 62.2 | 30.8[c] |

TABLE 2-continued

Percent of Children with Type A and B Tympanogram and
Passing and Failing Diagnostic Hearing Testing who
Selected the Correct Picture for Each Sentence Stimulus

| STIMULI<br>Test Sentences | TYMPANOGRAM RESULT | | HEARING DIAGNOSTIC RESULT | |
|---|---|---|---|---|
| | Type A %<br>Corr<br>(n = 34) | Type B %<br>Corr<br>(n = 18) | Pass %<br>Corr<br>(n = 37) | Fail %<br>Corr<br>(n = 13)[a] |
| 58. Run with me. | 55.9 | 44.4 | 59.5 | 38.5 |

[a]Two children did not have diagnostic hearing results.
[b]$p < .05$, 1t; Fisher's Exact Test for Type A vs. Type B and Hearing Pass vs. Fail.
[c]$p < .10$, 1t; Fisher's Exact Test for Type A vs. Type B and Hearing Pass vs. Fail.

Language scores were created for each word in the following way: if the morpheme was incorrectly spoken or the morpheme was correctly spoken but all phonemes were incorrect, the word was scored as "incorrect" (score=0); if the morpheme and at least one phoneme were repeated correctly, the word was scored as "correct" (score=1). For sentences, all of which contained multiple morphemes, the percentage of correct repetitions of morphemes in the sentence was used as the language score.

Language scores for words and sentences for the Type A and B tympanogram and hearing pass and fail groups were examined. Group comparisons were significant ($p < 0.05$) for 11 of the 28 words (39%) and 16 of the 23 sentences (70%).

The foregoing is illustrative of the present invention, and not to be construed as limiting thereof. The invention is defined by the following claims, with equivalents of the claims to be included therein.

That which is claimed is:

1. A human communication test apparatus for screening hearing, speech, and language functions in a human subject, comprising:
   (a) sound generator means for presenting verbal auditory stimuli to a subject, which stimuli may be vocalized by said subject;
   (b) video generator means operatively associated with said sound generator means for presenting a plurality of visual scenes to said subject in conjunction with the presentation of any one of said verbal auditory stimuli, one of said scenes corresponding to said verbal auditory stimulus presented;
   (c) first scoring means operatively associated with said video generator means for providing an evaluation of whether said subject can identify said scene corresponding to said verbal auditory stimulus;
   (d) second scoring means operatively associated with said sound generator means for providing an evaluation of a vocalization by said subject of said verbal auditory stimulus presented; and
   (e) second sound generator means for presenting masking noise concurrently with said verbal auditory stimulus to said subject.

2. An apparatus according to claim 1, wherein said scoring means further comprises means for scoring said subject's vocalization of individual sound units of said verbal auditory stimulus.

3. An apparatus according to claim 1, further comprising storage means operatively associated with said first and second scoring means for storing the evaluation of whether said subject can identify said scene corresponding to said verbal auditory stimulus and for storing the evaluation of said subject's vocalization of said verbal auditory stimulus.

4. An apparatus according to claim 1, further comprising a processor for determining whether said subject should receive further diagnostic tests of hearing, speech, and language based upon said evaluation of whether said subject can identify said scene corresponding to said verbal auditory stimulus and said evaluation of said subject's vocalization of said verbal auditory stimulus.

5. An apparatus according to claim 4, wherein said processor includes an empirically based model of actual clinical experience to determine whether said subject should receive further diagnostic tests.

6. An apparatus according to claim 4, further comprising a data file of actual clinical experience, wherein said apparatus includes means communicating with said data file for adding said evaluation of whether said subject can identify said scene corresponding to said verbal auditory stimulus and said evaluation of said subject's vocalization of said verbal auditory stimulus presented, and wherein said empirically based model of actual clinical experience is derived from said data file.

7. An apparatus according to claim 4, further comprising means for recording demographic data concerning said subject, and wherein said processor uses said demographic data for determining whether said subject should receive further diagnostic tests.

8. An apparatus according to claim 1, wherein said verbal auditory stimuli include stimuli comprising a test word, wherein one of said scenes corresponds to said test word, and wherein at least one other of said scenes corresponds to a second word differing in sound from said test word by a single phoneme only.

9. An apparatus according to claim 1, wherein said verbal auditory stimuli including stimuli comprising a test phrase, wherein one of said scenes corresponds to said test phrase, and wherein at least one other of said scenes corresponds to a second phrase differing in sound from said test phrase by a single morpheme only.

10. A human communication test apparatus for screening hearing and language functions in a human subject, comprising:
   (a) sound generator means for presenting verbal auditory stimuli to a subject;
   (b) video generator means operatively associated with said sound generator means for presenting a plurality of visual scenes to said subject in conjunction with the presentation of any one of said verbal auditory stimuli, one of said scenes corresponding to said verbal auditory stimulus presented;
   (c) scoring means operatively associated with said video generator means for providing an evaluation of whether said subject can identify said scene corresponding to said verbal auditory stimulus; and (d) second sound generating means for presenting masking noise concurrently with said verbal auditory stimulus to said subject.

11. An apparatus according to claim 10, further comprising storage means operatively associated with said scoring means for storing the evaluation of whether said subject can identify said scene corresponding to said verbal auditory stimulus.

12. An apparatus according to claim 10, further comprising a data file of actual clinical experience, wherein said apparatus includes means communicating with said data file for adding said evaluation of whether said subject can identify said scene corresponding to said verbal auditory stimulus, and wherein said empirically based model of actual clinical experience is derived from said data file.

13. An apparatus according to claim 10, further comprising means for recording demographic data concerning said subject, wherein said processor uses said demographic data for determining whether said subject should receive further diagnostic tests.

14. An apparatus according to claim 10, wherein said verbal auditory, stimuli include stimuli comprising a test word, wherein one of said scenes corresponds to said test word, and wherein at least one other of said scenes corresponds to a second word differing in sound from said test word by a single phoneme only.

15. An apparatus according to claim 10, wherein said verbal auditory stimuli include stimuli comprising a test phrase, wherein one of said scenes corresponds to said test phrase, and wherein at least one other of said scenes corresponds to a second phrase differing in meaning from said test phrase by a single morpheme only.

16. An apparatus according to claim 10, further comprising a second sound generator means for presenting masking noise with said verbal auditory stimulus to said subject.

17. An apparatus according to claim 10, further comprising a processor for determining whether said subject should receive further diagnostic tests of hearing and language based upon said evaluation of whether said subject can identify said scene corresponding to said verbal auditory stimulus; wherein said processor uses an empirically based model of actual clinical experience for determining whether said subject should receive further diagnostic tests.

18. A method of screening communication functions in a human subject, comprising:

(a) concurrently presenting (i) masking noise and (ii) a verbal auditory stimulus to said subject;

(b) scoring a response to said verbal auditory stimulus; said response selected from the group consisting of:

(i) said subject's vocalization of said verbal auditory stimulus presented;

(ii) said subject's identification of one scene from a plurality of scenes, wherein only said one scene corresponds to said verbal auditory stimulus presented; and (iii) both (i) and (ii) above;

(c) cyclically repeated steps (a) through (b) above to provide an evaluation of said subject's response to said verbal auditory stimuli; and then (d) determining whether said subject should receive further diagnostic tests of communicative development based upon said evaluation.

19. A method according to claim 18, wherein said step of scoring the subject's said vocalization response to said verbal auditory stimulus includes scoring said subject's vocalization of individual sound units of said verbal auditory stimulus.

20. A method according to claim 18, wherein at least one other of said scenes corresponds to a word or phrase differing in sound from said verbal auditory stimuli by a single sound unit only.

21. A method according to claim 18, further comprising the step of recording demographic data concerning said subject, and wherein said step of determining whether said subject should receive further diagnostic tests employs said demographic data.

22. A method of testing hearing and language functions in a human subject, comprising:

(a) presenting a verbal auditory stimuli to a subject, wherein said verbal auditory stimuli is selected from the group consisting of test words and test phrases; and (b) presenting a plurality of visual scenes to said subject, wherein one scene corresponds to said verbal auditory stimuli; and wherein at least one other of said scenes corresponds to a word or phrase differing in sound from said verbal auditory stimulus by a single sound unit only;

(c) detecting whether or not said subject can identify said one scene which corresponds to said verbal auditory stimuli; and (d) presenting masking noise concurrently with said verbal auditory stimulus to said subject.

23. A method according to claim 22, wherein said verbal auditory stimuli include stimuli comprising a test word, wherein one of said scenes corresponds to said test word, and wherein at least one other of said scenes corresponds to a second word differing in sound from said test word by a single phoneme only.

24. A method according to claim 22, wherein said verbal auditory stimuli include stimuli comprising a test phrase, wherein one of said scenes corresponds to said test phrase, and wherein at least one other of said scenes corresponds to a second phrase differing in meaning from said test phrase by a single morpheme only.

* * * * *

UNITED STATES PATENT AND TRADEMARK OFFICE
CERTIFICATE OF CORRECTION

PATENT NO. : 5,303,327

DATED : 12 April 1994

INVENTOR(S) : Raymond A. Sturner, James H. Heller; Michael D. Feezor

It is certified that error appears in the above-identified patent and that said Letters Patent is hereby corrected as shown below:

Column 8, Line 5, after by insert --MetraByte--.

Column 12, Table 1, 9. seal, correct "61.6$^b$" to read --61.1$^b$--.

Signed and Sealed this

Twenty-third Day of August, 1994

Attest:

BRUCE LEHMAN

Attesting Officer    Commissioner of Patents and Trademarks